(12) United States Patent
Sekiguchi et al.

(10) Patent No.: US 6,632,677 B1
(45) Date of Patent: Oct. 14, 2003

(54) AIR SHUTOFF AGENT FOR AQUEOUS REAGENT AND AQUEOUS SPECIMEN, AND METHOD FOR STORING AQUEOUS REAGENT AND AQUEOUS SPECIMEN WITH STABILITY

(75) Inventors: Masahiro Sekiguchi, Ryugasaki (JP); Toshikatsu Abe, Ryugasaki (JP); Koji Ushizawa, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/786,749

(22) PCT Filed: Sep. 9, 1999

(86) PCT No.: PCT/JP99/04906

§ 371 (c)(1),
(2), (4) Date: Mar. 9, 2001

(87) PCT Pub. No.: WO00/16104

PCT Pub. Date: Mar. 23, 2000

(30) Foreign Application Priority Data

Sep. 14, 1998 (JP) ............................................. 10-260408

(51) Int. Cl.⁷ ............................................... G01N 31/00

(52) U.S. Cl. ................................ 436/18; 436/8; 436/60; 436/139; 436/141; 436/174; 436/176; 252/408.1

(58) Field of Search .................................. 436/8, 18, 60, 436/139, 141, 174, 176, 183; 252/408.1

(56) References Cited

U.S. PATENT DOCUMENTS 6,194,452 B1 * 2/2001 Murad .......................... 514/474

FOREIGN PATENT DOCUMENTS

| JP | 4-161855 | * | 6/1992 |
|----|----------|---|--------|
| JP | 6-273425 |   | 9/1994 |
| JP | 6-324050 |   | 11/1994 |
| JP | 10-185927 |   | 7/1998 |
| JP | 11-155593 | * | 6/1999 |

* cited by examiner

Primary Examiner—Maureen M. Wallenhorst
(74) Attorney, Agent, or Firm—Oblon, Spivak, McClelland, Maier & Neustadt, P.C.

(57) ABSTRACT

An air-barrier agent for an aqueous reagent or an aqueous specimen having as an effective component a mixture of a chain hydrocarbon and a silicone oil immiscible with the aqueous reagent as well methods of using and making the same.

17 Claims, 2 Drawing Sheets

Reference product

Present invention product

Reference product　　　　　　Present invention product

AIR SHUTOFF AGENT FOR AQUEOUS REAGENT AND AQUEOUS SPECIMEN, AND METHOD FOR STORING AQUEOUS REAGENT AND AQUEOUS SPECIMEN WITH STABILITY

TECHNICAL FIELD

The present invention relates to an air shutoff agent (air-barrier agent) used to stably store a reagent component or a substance to be analyzed by preventing an aqueous reagent or an aqueous specimen from being in contact with air. More particularly, the present invention relates to an air-barrier agent which is used to stably store a reagent component or a substance to be analyzed by layering the air-barrier agent over the surface of an aqueous reagent or aqueous specimen, and which does not soil a measuring section of an autoanalyzer during repeated use. The present invention also relates to a method for stably storing an aqueous reagent or an aqueous specimen using the air-barrier agent.

BACKGROUND ART

At present, reagents used for clinical examinations are usually supplied as a liquid or in freeze-dried form. Liquid reagents are used as is and freeze-dried reagents are dissolved when used for measurement. Generally, these reagents are allowed to stand unsealed in a cool place during analysis using an autoanalyzer or during preservation.

Reagents in an unsealed state may exhibit insufficient stability. Specifically, measured values or sensitivity may decrease over time depending on the properties of the reagent component. Moreover, coloration of the reagent or an increase in blank values frequently occurs. Therefore, accuracy and precision which are the most important properties for diagnostic reagents may decrease over time. For example, a reagent using an OCPC method is used for determination of calcium in living body fluid. Since monoethanolamine used as a base buffer solution of the reagent absorbs $CO_2$ in air, the pH of the solution is shifted to the acidic side, thereby affecting the measured values.

Depending on the type of specimen, a component to be analyzed may be easily oxidized by oxygen in air. Such a specimen must be prevented from being in contact with air immediately after sampling in order to prevent oxidization from occurring.

As technology for solving the above problems relating to reagents and specimens, the present inventors have proposed a method of stabilizing a reagent or the like by layering an air-barrier agent, which is immiscible with the reagent and has a specific gravity lower than that of the reagent over the reagent or the like (Japanese Patent Application Laid-open No. 185927/1998).

This method can be applied to various reagents and specimens. However, a problem may occur when this method is applied to a reagent used in an autoanalyzer. Specifically, the air-barrier agent layered over the reagent adheres to a reagent suction/regurgitate nozzle of the autoanalyzer. This may cause a slight amount of the air-barrier agent to flow into a reaction vessel together with the reagent when discharging the reagent into the reaction vessel. In the case of a recently used reaction vessel made of a plastic, the air-barrier agent adheres to the wall of the reaction vessel, thereby soiling the surface of the wall by itself and by interaction with other substances.

Therefore, there has been a demand for an air-barrier substance which does not soil a reaction vessel made of any material of an autoanalyzer even if the air-barrier agent flows into the reaction vessel when discharging the reagent over which the air-barrier agent is layered.

DISCLOSURE OF THE INVENTION

The present inventors have conducted extensive studies to solve these problems. As a result, the present inventors have found that an air-barrier agent containing a chain (linear or branched) hydrocarbon and silicone oil does not soil a reaction vessel due to small affinity thereto, and can be widely used for a reaction vessel made of any material. This finding has led to the completion of the present invention.

Specifically, the present invention provides an air-barrier agent for an analytical reagent or specimen comprising a mixture of a chain hydrocarbon and silicone oil which is immiscible with an aqueous reagent or an aqueous specimen and has a specific gravity lower than that of the reagent or specimen.

The present invention also provides a method for stably storing an aqueous analytical reagent or an aqueous specimen comprising layering the above mixture over the surface of the aqueous analytical reagent or aqueous specimen.

BEST MODE FOR CARRYING OUT THE INVENTION

Figure 1:
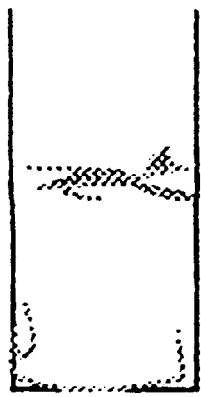
FIG. 1 is a comparative view showing soiling conditions in the case of using a present invention product 1 and a reference product 1.
Figure 1:
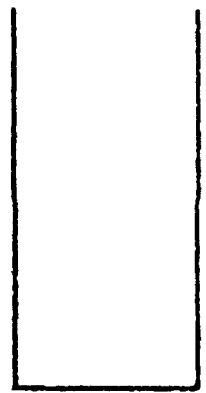

In the present invention, a mixture of a chain hydrocarbon and silicone oil is used as the air-barrier agent. This mixture must be immiscible with an objective aqueous reagent or aqueous specimen (hereinafter called "reagent or specimen") and have a specific gravity (density) lower than that of the reagent or the like. Generally, the specific gravity of a reagent such as a reagent used for clinical examination is about 1. Therefore, the specific gravity of the mixture is preferably about 0.7–0.95, and particularly preferably about 0.86 or less. It is preferable that the mixture be a liquid at room temperature and have a specific gravity differing from that of the reagent in the range from about 0.05 to 0.3.

As the chain hydrocarbon among the components of the mixture, a chain hydrocarbon with a viscosity of less than 37 cSt and a flash point of 46° C. or more is used. Specific examples include octane, nonane, decane, undecane, dodecane, tridecane, tetradecane, and the like. Of these, a chain hydrocarbon with a flash point of 80° C. or more is preferable in view of ease in handling in practical application.

As the silicone oil which is the other component of the mixture, a polyalkylsiloxane, polyalkylphenylsiloxane, polyalkyl hydrogen siloxane, and the like can be used. It is preferable to use a linear dimethylpolysiloxane which is commercially available as silicone oil, which is a mixture of linear dimethylpolysiloxanes having different molecular weights and shown by the following formula in which n is various values.

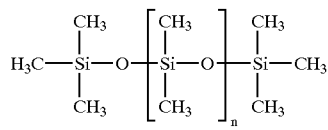

As the linear dimethylpolysiloxane, linear dimethylpolysiloxanes having various kinematic viscosities of 100 cSt or less are known. The kinematic viscosity of the linear dimethylpolysiloxane is preferably about 1.5–100 cSt, and still more preferably 3–50 cSt.

The mixture may be prepared using the chain hydrocarbon and the silicone oil so that the silicone oil content in the mixture is 1–99%, preferably about 10–90%, and still more preferably 30–50%.

When using the mixture of the chain hydrocarbon and the silicone oil thus prepared as the air-barrier agent, the mixture may be layered over the surface of an aqueous reagent or an aqueous specimen which is in the form of a liquid or a solution obtained by dissolving a freeze-dried product. There are no specific limitations to the amount of the air-barrier agent to be used. It is preferable to use the air-barrier agent in an amount from 0.03 ml to 1.0 ml per 1 $cm^2$ of the surface of the reagent (surface in contact with air with no air-barrier agent layer formed).

A stable reagent unit may be prepared by filling a container with a liquid reagent using a conventional method and forming a layer of the mixture of the chain hydrocarbon and the silicone oil on the upper surface of the reagent. Alternatively, a stable reagent unit may be prepared by adding the mixture of the chain hydrocarbon and the silicone oil to a container and forming a layer of the mixture by injecting a liquid reagent into the container. As a material for the container for the reagent unit, glass, metals, plastics, and the like can be used. It is preferable to use a container which does not allow air to permeate and has a narrow opening.

In the present invention, it is important to use the reagent for tests or examinations by removing only the reagent or the like from the container using a reagent suction nozzle of an autoanalyzer, pipette, needle, or the like without mixing the reagent or specimen with the air-barrier agent.

If surfactants or other materials which may emulsify the air-barrier agent are present in the reagent, the effect of the present invention may become insufficient. If any components of the reagent having some function in the measurement have extremely high affinity to the air-barrier agent, such components if moved to the air-barrier agent layer may impair the effects of the reagent. Care should be taken to prevent such occurrence.

INDUSTRIAL APPLICABILITY

The air-barrier agent of the present invention prevents the reagent or the like from being in contact with air by layering the air-barrier agent over the surface of the reagent or the like. Therefore, the air-barrier agent can provide the reagent or the like with excellent storage stability, thereby enabling measurement for a long period of time.

The air-barrier agent of the present invention does not soil materials which may be used for a reaction vessel of an autoanalyzer, such as glass, quartz, plastics (polypropylene, polystyrene, methacrylate, polymethylpentene, and the like) Therefore, the air-barrier agent can be repeatedly used in the autoanalyzer.

As described above, the present invention can effectively prevent the reagent or the like from being in contact with air and does not soil the reaction vessel of the autoanalyzer. Therefore, the present invention can be advantageously applied to a reagent used for analysis using the autoanalyzer, such as an alkaline phophatase measuring reagent, calcium measuring reagent, bile acid measuring reagent, creatinine measuring reagent, and triglyceride measuring reagent or specimen.

EXAMPLES

The present invention will be described in detail by examples, which should not be construed as limiting the present invention.

Example 1

Application to Calcium Measuring Reagent

Isoparaffin and silicone (polydimethylsiloxane, 200R FLUID, kinematic viscosity: 5 cSt, manufactured by Aldrich) were mixed at a ratio of 6 to 4 to prepare an air-barrier agent (present invention product 1).

This air-barrier agent was layered over a reagent 1 of a calcium measuring reagent according to a composition given below. Using a Hitachi 7170 Automatic Analyzer, 150 µl of the reagent 1 was added to 4 µl of a specimen, and the mixture was stirred and then incubated at 37° C. for five minutes. After the addition of a reagent 2, the mixture was incubated at 37° C. for five minutes. The absorbance of the mixture at 600 nm was then measured.

The measurement was repeated four times continuously using the same reaction vessel (made of polymethylpentene plastic). After the measurements, the degree of soiling of the reaction vessel was observed with the naked eye and evaluated according to standards given below. FIG. 1 shows the soiling conditions.

As a reference, a reference product 1 prepared using a reagent 1 of the present invention product containing only isoparaffin in instead of the 6:4 mixture of isoparaffin and silicone was used.

(Reagent Composition of Present Invention Product 1)
  Reagent 1
  Monoethanolamine: 0.5 M
  Mixture of isoparaffin and silicone (ratio=6:4): 3 ml
  (Per 70 ml bottle)
  Reagent 2
  o-Cresolphthalein complexon: 0.13 mM
  8-Hydroxy-5-sulfonic acid: 10 mM
  Acetic acid buffer solution: 0.24 M (pH 6.0)
(Reagent 1 of reference product 1)
  Monoethanolamine: 0.5 M
  Isoparaffin: 3 ml
  (Per 70 ml bottle)
(Evaluation Standards for Soiling of Reaction Vessel)

| Evaluation | Condition |
|---|---|
| − | No soiling |
| ± | Very slight soiling |
| + | Slight soiling |
| ++ | Soiled |
| +++ | Soiled significantly |

(Results)

The evaluation results of the soiling of the reaction vessel are shown in Table 1.

TABLE 1

| Reagent | Degree of soiling |
| --- | --- |
| Present invention product 1 | – |
| Reference product 1 | +++ |

As is clear from these results, the reaction vessel exhibited no soiling after four continuous measurements using the present invention product 1. On the contrary, the inner wall of the reaction vessel was soiled when using the reference product 1.

As shown in FIG. 1, no soiling was recognized in the reaction vessel after measurements using the present invention product 1 (right in FIG. 1). On the contrary, soiling was recognized at the center of the reaction vessel when using the reference product (left in FIG. 1).

As described above, the air-barrier agent of the present invention which uses the mixture of a chain hydrocarbon and silicone does not cause the reaction vessel to be soiled during repeated use.

Example 2

Application to Alkaline Phosphatase Measuring Reagent

Each mixture of a chain hydrocarbon and silicone oil (air-barrier agent) was layered over a reagent 1 of an alkaline phosphatase measuring reagent having a composition given below. The mixture was allowed to stand unsealed in a cool place (8° C.). Alkaline phosphatase activity in human blood serum was sequentially measured using this alkaline phosphatase measuring reagent according to a method given below. Changes in the measured values were compared and examined. The results are shown in Table 2.

(Reagent Composition)

Reagent 1

Ethylaminoethanol buffer solution: 1.0 M (pH 9.9)

Magnesium chloride: 0.5 mM

Air-barrier agent* (see Table 2): 0.2 ml/cm$^2$

Reagent 2 p-Nitrophenylphosphate: 15 mM

* Amount added per 1 cm2 of open area of reagent container (hereinafter the same)

(Measuring Method)

260 μl of the reagent 1 was added to 4 μl of a specimen. The mixture was stirred and then incubated at 37° C. for five minutes. After the addition of 130 μl of the reagent 2, the mixture was stirred. Using a reagent blank as a reference, changes in absorbance of the mixture at a wavelength of 450 nm were measured at 37° C. from two to five minutes using a Hitachi 7150 Automatic Analyzer. A physiological saline solution was used as the reagent blank. The alkaline phosphatase (ALP) activity was calculated from a conversion factor derived from a molecular extinction coefficient of p-nitrophenylphosphate, which was the reaction product, and the variation in absorbance.

(Results)

TABLE 2

| Air-barrier agent | ALP measured value (U/l) | | | |
| --- | --- | --- | --- | --- |
| | 0 day | 7 days | 14 days | 22 days |
| Undecane + silicone | 444 | 442 | 443 | 442 |
| Dodecane + silicone | 442 | 444 | 441 | 443 |
| Tridecane + silicone | 442 | 441 | 443 | 442 |
| Tetradecane + silicone | 443 | 441 | 442 | 444 |
| Isoparaffin + silicone | 443 | 444 | 442 | 442 |
| No addition (reference) | 443 | 385 | 329 | 237 |

As is clear from these results, the measured values significantly decreased over time in the case where the air-barrier agent was not added (reference). On the contrary, the measured values showed no decrease after 22 days in the case where the air-barrier agent of the present invention was used. Specifically, the alkaline phosphatase activity can be precisely measured for a long period of time by using the air-barrier agent of the present invention.

Example 3

Application to Bile Acid Measuring Reagent

A mixture of undecane and silicone (ratio=6:4) was added to a reagent 2 of a bile acid measuring reagent as an air-barrier agent according to a composition given below (present invention product 2). The mixture was allowed to stand unsealed in a cool place. A bile acid standardized solution (50 μM) was sequentially measured using the reagent 2 of the bile acid measuring reagent. Changes in the measurement sensitivity was compared and examined. The results are shown in Table 3. As a reference, a reagent 2 excluding the above undecane/silicone mixture (reference product 2) was used.

(Reagent Composition)

Reagent 1

Oxidized β-thionicotinamide adenine dinucleotide: 0.99 mg/ml

Glycine buffer solution: 0.03 M (pH 4.0)

Reagent 2

Reduced β-nicotinamide adenine dinucleotide: 5.04 mg/ml

3α-Hydroxysteroid dehydrogenase: 9.5 U/ml

Mixture of undecane and silicone: 0.3 ml/cm$^2$

Diethanolamine buffer solution: 0.2 M (pH 9.2)

(Measuring Method)

260 μl of the reagent 1 was added to 3 μl of a specimen. The mixture was incubated at 37° C. for five minutes. After the addition of 130 μl of the reagent 2, the mixture was stirred. Using a reagent blank as a reference, changes in absorbance of the mixture at a wavelength of 405 nm was measured at 37° C. from one to three minutes using a Hitachi 7150 Automatic Analyzer. A physiological saline solution was used as the reagent blank.

(Results)

TABLE 3

| Preservation | Bile acid measurement sensitivity (mAbs/min) | |
| --- | --- | --- |
| | Present invention product 2 | Reference product 2 |
| 0 day | 34 | 34 |
| 8 days | 33 | 24 |
| 16 days | 33 | 22 |
| 24 days | 32 | 19 |

As is clear from these results, the measurement sensitivity significantly decreased over time in the case where the air-barrier agent was not added (reference product 2). On the contrary, the measurement sensitivity showed no decrease in the case where the air-barrier agent of the present invention was used (present invention product 2). Specifically, bile acid can be precisely measured for a long period of time by the method using the air-barrier agent of the present invention.

Example 4

Application to Creatinine Measuring Reagent

A mixture of tridecane and silicone (ratio=6:4) was added to a reagent 1 of a creatinine measuring reagent as an air-barrier agent (present invention product 3) according to a composition given below. The mixture was allowed to stand unsealed in a cool place. A creatinine standardized solution (10.0 mg/dl) was sequentially measured using the reagent 1 of the creatinine measuring reagent. Variation in the measurement sensitivity was compared and examined. The results are shown in Table 4. As a reference, a reagent 1 excluding the above tridecane/silicone mixture (reference product 3) was used.

(Reagent Composition)
Reagent 1
Sodium hydroxide: 0.2 M
Mixture of tridecane and silicone: 0.2 ml/cm$^2$
Reagent 2
2,4,6-Trinitrophenol: 28.4 mM
(Measuring Method)
300 μl of the reagent 1 was added to 15 μl of a specimen. The mixture was stirred and then incubated at 37° C. for five minutes. After the addition of 75 μl of the reagent 2, the mixture was stirred and then incubated at 37° C. for five minutes. Using a reagent blank as a reference, absorbance at a wavelength of 505 nm was measured using a Hitachi 7150 Automatic Analyzer. A physiological saline solution was used as the reagent blank.
(Results)

TABLE 4

| Preservation | Creatinine measurement sensitivity (mAbs/100 mg/dl) | |
| --- | --- | --- |
| | Present invention product 3 | Reference product 3 |
| 0 day | 931 | 930 |
| 8 days | 930 | 371 |
| 16 days | 931 | 94 |

As is clear from these results, the measurement sensitivity significantly decreased over time in the case where the air-barrier agent was not added (reference product 3). On the contrary, the measurement sensitivity showed no decrease in the case where the air-barrier agent of the present invention was used (present invention product 3). Specifically, creatinine can be precisely measured for a long period of time by the method using the air-barrier agent of the present invention.

Example 5

Application to Triglyceride Measuring Reagent

Figure 2:
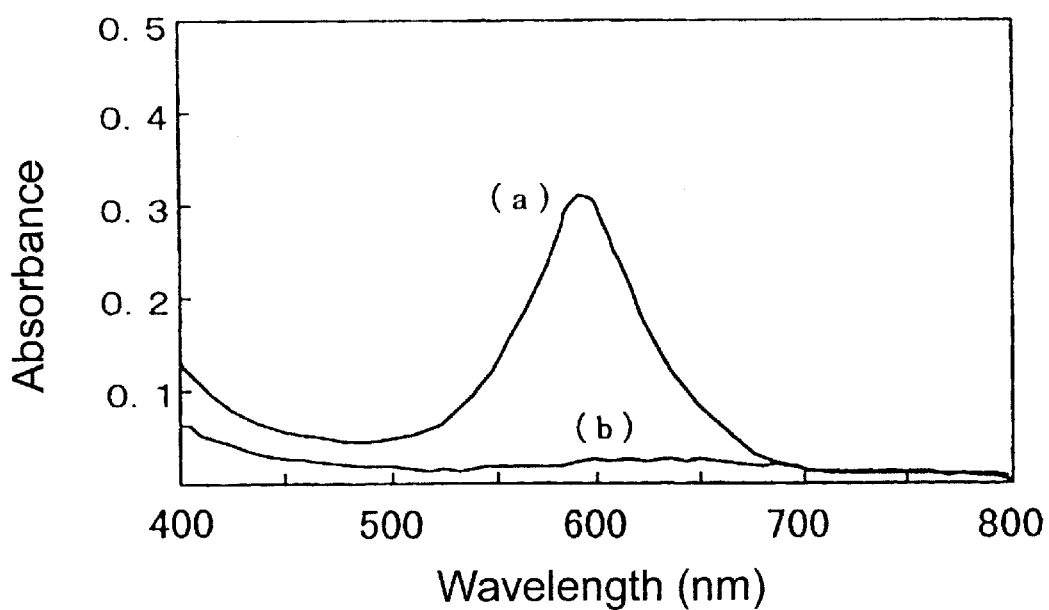
FIG. 2 is a view comparatively showing coloration over time of a reagent 1 of a triglyceride measuring reagent containing a color developer to which an air-barrier agent of the present invention is added and the reagent 1 containing no air-barrier agent.

An air-barrier agent (mixture of tetradecane and silicone (ratio=6:4)) was added to a reagent 1 containing a color developer of a triglyceride measuring reagent (present invention product 4) according to a composition given below. This product was allowed to stand unsealed in a cool place. The degree of coloration over time of the reagent 1 was compared with a reagent 1 excluding the above tetradecane/silicone mixture (reference product 4) using a measuring method given below. The results are shown in FIG. 2.

(Reagent Composition)
Reagent 1
Glycerol kinase: 900 U/l
Glycerol 3-phosphate oxidase: 3800 U/l
Peroxidase: 1950 U/l
Sodium 3,5-dimethoxy-N-ethyl-N-(2-hydroxy-3-sulfopropyl) aniline: 1.8 mM
Mixture of tetradecane and silicone: 0.2 ml/cm$^2$
Good buffer solution: 0.2 M (pH 6.5)
(Measuring Method)
10 ml of the reagent 1 was allowed to stand unsealed in a cool place for 40 days. Using a reagent blank as a reference, an absorption spectrum of the reagent at a wavelength from 400 nm to 800 nm was measured using a Beckman DU640 spectrophotometer. As the reagent blank, distilled water was used.
(Results)
As is clear from FIG. 2, in the case where the air-barrier agent was not added (reference product 4), oxygen in air was absorbed into the reagent, thereby causing oxidization of the color developer to proceed. As shown in FIG. 2(a), significant blue coloration exhibiting an absorption peak at 590 nm was observed.

On the contrary, in the case where the air-barrier agent was used (present invention product 4), no oxidization and coloration of the reagent were observed, as shown in FIG. 2(b) Specifically, according to the method using the air-barrier agent of the present invention, coloration of the triglyceride measuring reagent can be prevented, whereby the reagent can be stably stored for a long period of time.

What is claimed is:

1. An air-barrier agent comprising a mixture of a chain hydrocarbon and silicone oil, wherein the silicone oil has a kinematic viscosity of 100 cSt or less, and the mixture is immiscible with an aqueous reagent or an aqueous specimen, and has a specific gravity lower than that of the aqueous reagent or the aqueous specimen.

2. The air-barrier agent according to claim 1, wherein the chain hydrocarbon comprises at least one member selected from the group consisting of a liquid paraffin, isoparaffin, decane, undecane, dodecane, and tridecane.

3. The air-barrier agent according to claim 1, wherein the silicone oil comprises at least one member selected from the group consisting of polyalkylsiloxane, polyalkylphenylsiloxane, and polyalkyl hydrogen siloxane.

4. The air-barrier agent according to claim 3, wherein the content of the silicone oil is from 1 to 99% based on the mixture of the chain hydrocarbon and the silicone oil.

5. The air-barrier agent according to claim 1, wherein the mixture of the chain hydrocarbon and the silicone oil has a specific gravity of from 0.7 to 0.95.

6. The air-barrier agent according to claim 5, wherein the content of the silicone oil is from 1 to 99% based on the mixture of the chain hydrocarbon and the silicone oil.

7. The air-barrier agent according to claim 1, wherein the content of the silicone oil is from 1 to 99% based on the mixture of the chain hydrocarbon and the silicone oil.

8. The air-barrier agent according to claim 1, wherein the aqueous reagent comprises at least one, member selected from the group consisting of alkaline phosphatase measuring reagent, calcium measuring reagent, bile acid measuring reagent, creatinine measuring reagent and triglyceride measuring reagent.

9. The air-barrier agent according to claim 1, wherein the chain hydrocarbon and the silicone oil is present at a ratio of from 6 parts of the chain hydrocarbon to 4 parts of the silicone oil.

10. A method for storing an aqueous reagent or an aqueous specimen, comprising:
   contacting the air-barrier agent of claim 1 with the aqueous reagent or the aqueous specimen.

11. The method of claim 10, wherein the aqueous reagent comprises at least one member selected from the group consisting of alkaline phosphatase measuring reagent, calcium measuring reagent, bile acid measuring reagent, creatinine measuring reagent and triglyceride measuring reagent.

12. A composition comprising the air-barrier agent of claim 1; and an aqueous reagent or aqueous specimen.

13. The composition according to claim 12, wherein the air-barrier agent is present in an amount ranging from 0.03 to 1.0 ml per 1 $cm^2$ of surface area of the aqueous reagent or the aqueous specimen.

14. An autoanalyzer comprising the composition of claim 12, and a reaction vessel.

15. The autoanalyzer of claim 14, wherein the reaction vessel comprises at least one material selected from the group consisting of glass, quartz and plastic.

16. An autoanalyzer comprising the air-barrier agent of claim 1 and a vessel.

17. A method for storing an aqueous reagent, or an aqueous specimen comprising:
   contacting a mixture of a chain hydrocarbon and a silicone oil with the aqueous reagent or the aqueous specimen, wherein the silicone oil has a kinematic viscosity of 100 cSt or less, and the mixture is immiscible with the aqueous reagent or the aqueous specimen, and has a specific gravity lower than the aqueous reagent or aqueous specimen.

* * * * *